(12) United States Patent  
Horton, III

(10) Patent No.: US 6,730,265 B2
(45) Date of Patent: May 4, 2004

(54) AIR UV DISINFECTION DEVICE AND METHOD

(75) Inventor: Isaac B. Horton, III, Raleigh, NC (US)

(73) Assignee: Remote Light, Inc., Raleigh, NC (US)

( * ) Notice: Subject to any disclaimer, the term of this patent is extended or adjusted under 35 U.S.C. 154(b) by 0 days.

(21) Appl. No.: 10/016,217

(22) Filed: Nov. 2, 2001

(65) Prior Publication Data

US 2003/0086831 A1 May 8, 2003

(51) Int. Cl.[7] .................................................. A61L 2/00
(52) U.S. Cl. ..................... 422/24; 250/455.11; 422/22; 422/120; 422/121; 422/186.3
(58) Field of Search ........................... 422/22, 24, 121, 422/120, 186.3; 250/455.11

(56) References Cited

U.S. PATENT DOCUMENTS

| | | | |
|---|---|---|---|
| 5,426,308 A | * | 6/1995 | Sudduth et al. .......... 250/504 H |
| 5,614,151 A | * | 3/1997 | LeVay et al. ................ 422/24 |
| 5,706,376 A | | 1/1998 | Rykowski et al. |
| 5,833,740 A | | 11/1998 | Brais |
| 5,835,840 A | | 11/1998 | Goswami |
| 5,862,277 A | | 1/1999 | Riser et al. |
| 5,866,752 A | * | 2/1999 | Goozner ...................... 588/227 |
| 5,919,422 A | | 7/1999 | Yamanaka et al. |
| 5,925,320 A | | 7/1999 | Jones |
| 5,933,702 A | | 8/1999 | Goswami |
| 5,997,619 A | | 12/1999 | Knuth et al. |
| 6,051,194 A | | 4/2000 | Peill et al. |
| 6,053,968 A | | 4/2000 | Miller |
| 6,071,472 A | | 6/2000 | Caupin et al. |

* cited by examiner

Primary Examiner—Krisanne Thornton
(74) Attorney, Agent, or Firm—Glasgow Law Firm, PLLC

(57) ABSTRACT

An ultraviolet disinfection (UV) system for gases including a UV light-ready gas purifier having at least one portal in the gas purifier for receiving UV light input from a UV light source, which is removably connected to the gas purifier via a connector at the portal, and positioned to provide a focused, controllable UV light output that has at least one UV dose zone for providing effective sterilization of microorganisms and disinfection within an interior of the gas purifier. The light source is positioned within a housing that is external to the gas purifier and capable of being connected thereto via optical connectors, such as fiber optic transmission lines. A method for UV disinfection of the interior of gas purifiers is also included in the present invention.

74 Claims, 2 Drawing Sheets

AIR UV DISINFECTION DEVICE AND METHOD

BACKGROUND OF THE INVENTION

(1) Field of the Invention

The present invention relates generally to a system and method for ultraviolet disinfection and, more particularly, to a system and method for ultraviolet disinfection of air and other gases.

(2) Description of the Prior Art

It is well known in the art to use ultraviolet light (UV) for the disinfection treatment of air. Ultraviolet light, at the germicidal wavelength of 253.7 nanometers, alters the genetic (DNA) material in cells so that bacteria, viruses, molds, algae and other microorganisms can no longer reproduce. The microorganisms are considered dead, and the risk of disease from them is eliminated. As the air flows past the UV lamps in UV disinfection systems, the microorganisms are exposed to a lethal dose of UV energy. UV dose is measured as the product of UV light intensity times the exposure time within the UV lamp array. Microbiologists have determined the effective dose of UV energy to be approximately about 34,000 microwatt-seconds/cm2 needed to destroy pathogens as well as indicator organisms found in wastewater. Typical prior art disinfection systems and devices emit UV light at approximately 254 nm, which penetrates the outer cell membrane of microorganisms, passes through the cell body, reaches the DNA and alters the genetic material of the microorganism, destroying it without chemicals by rendering it unable to reproduce.

Ultraviolet light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of bacteria, viruses and other pathogens and thus destroys their ability to multiply and cause disease, effectively resulting in sterilization of the microorganisms. Specifically, UV "C" light causes damage to the nucleic acid of microorganisms by forming covalent bonds between certain adjacent bases in the DNA. The formation of these bonds prevents the DNA from being read correctly, and the organism is neither able to produce molecules essential for life process, nor is it able to reproduce. In fact, when an organism is unable to produce these essential molecules or is unable to replicate, it dies. UV light with a wavelength of approximately between about 250 to about 260 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Additionally, UV light can catalyze a variety of other chemical reactions, and the use of UV light with any one or combination of the plethora of available chemical catalyst generates numerous possible catalytic combinations that can be used to degrade organic particulate matter. A class of these photocatalyst, termed UV-activated dielectric semiconductors, includes Titanium Oxide; TiO2 (photo activation wavelength; not more than 388 nm), Tungsten Oxide; WO2 (photo activation wavelength; not more than 388 nm), Zinc Oxide; ZnO (photo activation wavelength; not more than 388 nm), Zinc Sulfide; ZnS (photo activation wavelength; not more than 344 nm) and Tin Oxide; SnO2 (photo activation wavelength; not more than 326 nm). In addition to these catalysts, other catalysts, such as PtTiO$_2$, are known.

In prior art air purification systems, particles, including, for example, household and atmospheric dust, lint, animal dander, food particles, tobacco smoke, aerosols, pollen, plant spores, and the like are removed from the air stream by filtration, trapping, electrostatic precipitation, and other means of arrest. Chemical compounds are removed by activated charcoal filtration. Additionally, particle and chemical compounds can be degraded by UV irradiation, or by oxidation by photocatalysts such as TiO$_2$.

While such conventional air cleaners are quite effective in arresting dust and other particles, if the filters or plates are not cleaned regularly to remove the deposited particles, there may be potential for microbial growth on the particles on the filters or collector plates. If microbial growth is present and is not removed through regular thorough cleaning, there is the possibility that bioaerosols such as fungal spores, bacteria and other allergens may be re-entrained into the air stream and circulated back into the occupied enclosure.

Several prior art inventions have used UV irradiation of the particle-arresting apparatus or the gas stream itself to sterilize resident microorganisms. These inventions, as described in U.S. Pat. No. 5,997,619, Dec. 7, 1999; Knuth, et al.; U.S. Pat. No. 5,925,320; Jul. 20, 1999; Jones; U.S. Pat. No. 5,833,740; Nov. 10, 1998; Brais; U.S. Pat. No. 6,053,968; Apr. 25, 2000; Miller. Although these prior art may have been adequate in arresting particulate matter and chemical compounds and inactivating microorganisms, they could not degrade them and thus needed frequent periodic maintenance to clean or replace the arresting devices.

It has now been found possible to degrade the particulate matter and other compounds by incorporating TiO2 or other photocatalyst in the arresting device and irradiating the TiO2 with UV light. The TiO2 catalyzes the breakdown of chemical molecules, both in arrested particles and in the vicinity of the arresting device. For example, U.S. Pat. Nos. 5,933,702; 5,919,422; and 5,835,840 use filters or supports charged or impregnated with TiO2, and by fitting these filters into ventilation systems in which they are also irradiated by a source of ultraviolet rays when they are not themselves exposed to a natural source of UV. Additionally, filters comprised of TiO2 may also be treated with undecylenic derivatives to aid in the decomposition of compounds. For example, Caupin et al. (U.S. Pat. No. 6,071,472) teach that the functioning of filters comprised of TiO2 and undecylenic derivatives proves to be surprisingly effective from the point of view of air quality and, in parallel, a very substantial increase in the lifetime of the filter is observed, the gradual soiling of which appears to be due essentially only to the retention of inorganic particles. However, this and the other prior art require a UV light source devoted to the device, and in no way teach that the UV light may be supplied by a fiber optic transmission line or similar using optical components to focus and control the light input.

U.S. Pat. No. 6,051,194 generally relates to a fixed bed photocatalytic reactor system that employs optical fibers as a means of remote light transmission to and support for a photocatalyst coating. The reactor enables batch treatment or continuous flow applications, e.g., for the destruction of gas or aqueous phase waste effluents contaminated with hydrocarbons or heavy metals. The reactor utilizes one or more optical fibers or rods stiffened or under tension to form non-flexible rod-like components that are positionally secured with respect to a reactor vessel and are spaced apart with respect to each other at a miniscule distance, preferentially 1.5 mm. It is critical to have stiffened, tensioned, or rod-like fibers without flexibility in order to establish and maintain the spaced-apart configuration. The fibers have a non-catalytic portion and a catalytic portion, wherein the catalytic portion comprises a TiO.sub.2 photocatalyst coating on the exposed fibers. Photocatalytic reactions are carried out by using the noncatalytic portion of the fibers to transmit light, e.g., UV, from a light source to the catalytic portion. Because of the efficiency of the fibers in light delivery to the catalytic portion of the coating, the light source may be located a relatively long distance from the catalytic portion of the fibers.

Such a reactor is not particularly well-suited for microfiltration of gas streams, as a filter in this fashion would need to be woven from a single or few fibers. If a multitude of transmission lines were used, these would have to be connected to the light source. Although such a configuration is technically possible, the resulting filter would be relatively expensive and also cumbersome to install and remove. Additionally, the reactor described by Peill et al. requires space between individual fibers to minimize the interfiber contact, as this contact can promote TiO2 coating delamination. Therefore, spacers are employed to maintain the fibers in a spaced-apart configuration. This spaced-apart configuration prevents an adequate physical filtration of the gas stream. Additionally, Peill et al. do not teach the use of optical components to focus and control the light input. As such, this prior art reactor teaches away from the configuration according to the present invention.

Thus, there remains a need for a low-maintenance, inexpensive UV purification system of air and other gases that purifies the gas stream, deactivates microorganisms in the proximity of the device, is self-cleaning and easily handled, and utilizes a remote UV light source.

SUMMARY OF THE INVENTION

The present invention is directed to a UV purification system and method for treating gas streams.

One object of the present invention is to provide a UV disinfection system for treating a gas stream configured and arranged to function effectively with at least one UV light source or lamp.

Another object of the present invention is to provide a UV-ready gas stream purifier that is designed to accept a UV light source input for the purpose of sterilization of microorganisms arrested by the purifier, albeit temporarily.

Another object of the present invention includes presentation of the UV light source detached from and remotely connectable with the gas purifier via fiber optic, UV transmission lines.

Another object of the present invention is to provide a UV-ready gas stream purifier that is designed to accept a UV light source input for the purpose of effecting degradation of arrested particles and compounds through the UV activation of a photocatalyst incorporated into the purifier.

Still another object of the present invention is to provide a method for providing ultraviolet disinfection (UV) within gas streams including selective activation and deactivation of at least one UV light-ready gas stream purifier having at least one portal in the particle arrestor for receiving UV light input from at least one light source, which is removably connected to the at least one UV light-ready gas stream purifier via a connector at the portal, and provides a focused, controllable UV light output that has at least one UV dose zone for providing effective sterilization of microorganisms and disinfection within an interior of the gas stream purifier.

Accordingly, one aspect of the present invention is to provide a UV disinfection system for treating a gas stream configured and arranged to function effectively with at least one UV light source or lamp.

Another aspect of the present invention is to provide a UV-ready gas stream purifier that is designed to accept a UV light source input for the purpose of sterilization of microorganisms arrested by the particle arrestor, albeit temporarily.

Another aspect of the present invention is to provide presentation of the UV light source detached from and remotely connectable with the gas stream purifier via fiber optic, UV transmission lines and including the use of optical components.

Still another aspect of the present invention is to provide a UV-ready gas stream purifier that is designed to accept a UV light source input for the purpose of effecting degradation of arrested particles and compounds through the UV activation of a photocatalyst incorporated into the gas stream purifier.

Still another object of the present invention is to provide a method for providing ultraviolet disinfection (UV) within gas streams including selective activation and deactivation of at least one UV light-ready gas stream purifier having at least one portal in the gas stream purifier for receiving UV light input from at least one light source, which is removably connected to the at least one UV light-ready gas stream purifier via a connector at the portal, and provides a focused, controllable UV light output that has at least one UV dose zone for providing effective sterilization of microorganisms and disinfection within an interior of the gas stream purifier.

These and other aspects of the present invention will become apparent to those skilled in the art after a reading of the following description of the preferred embodiment according to the present invention when considered with the drawings.

DETAILED DESCRIPTION OF THE PREFERRED EMBODIMENTS

Figure 1:
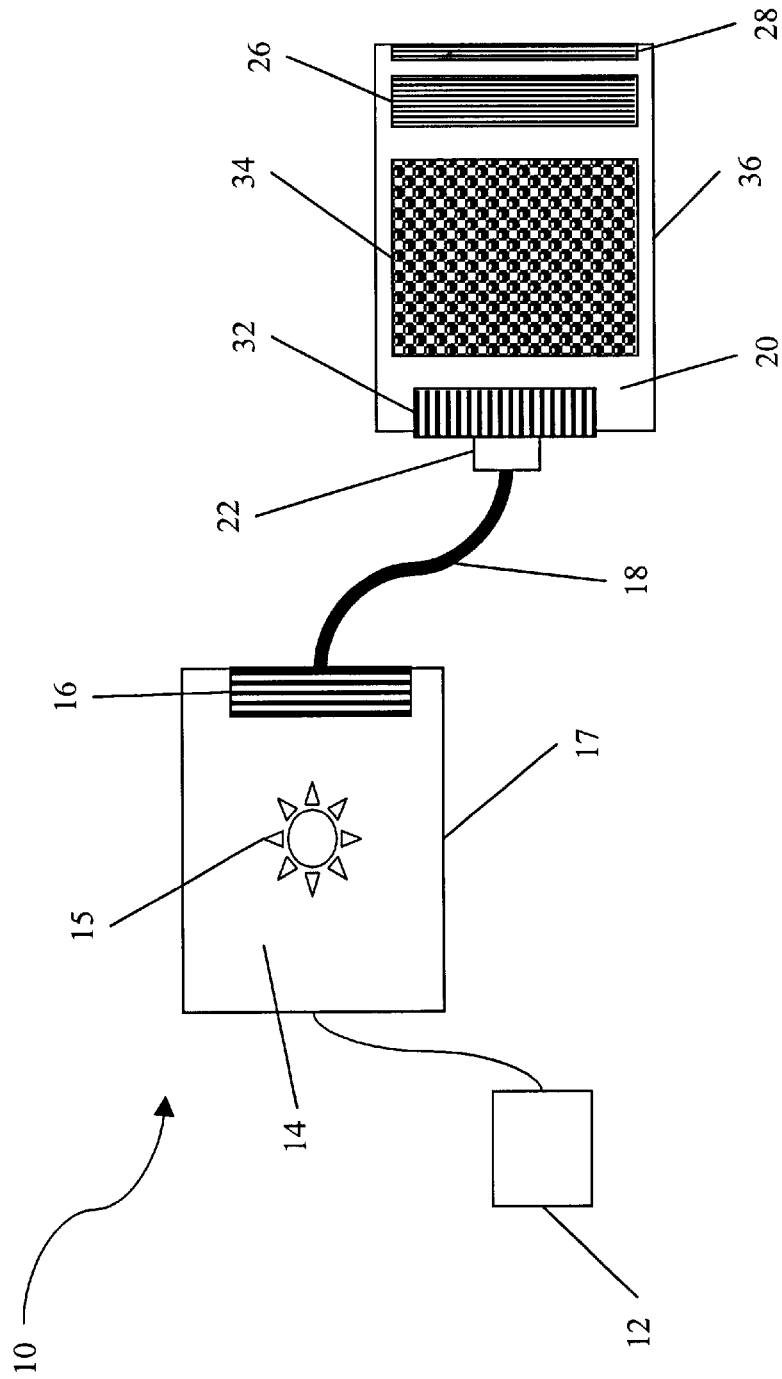
FIG. 1 is a schematic diagram of the complete UV air disinfection system.
Figure 2:
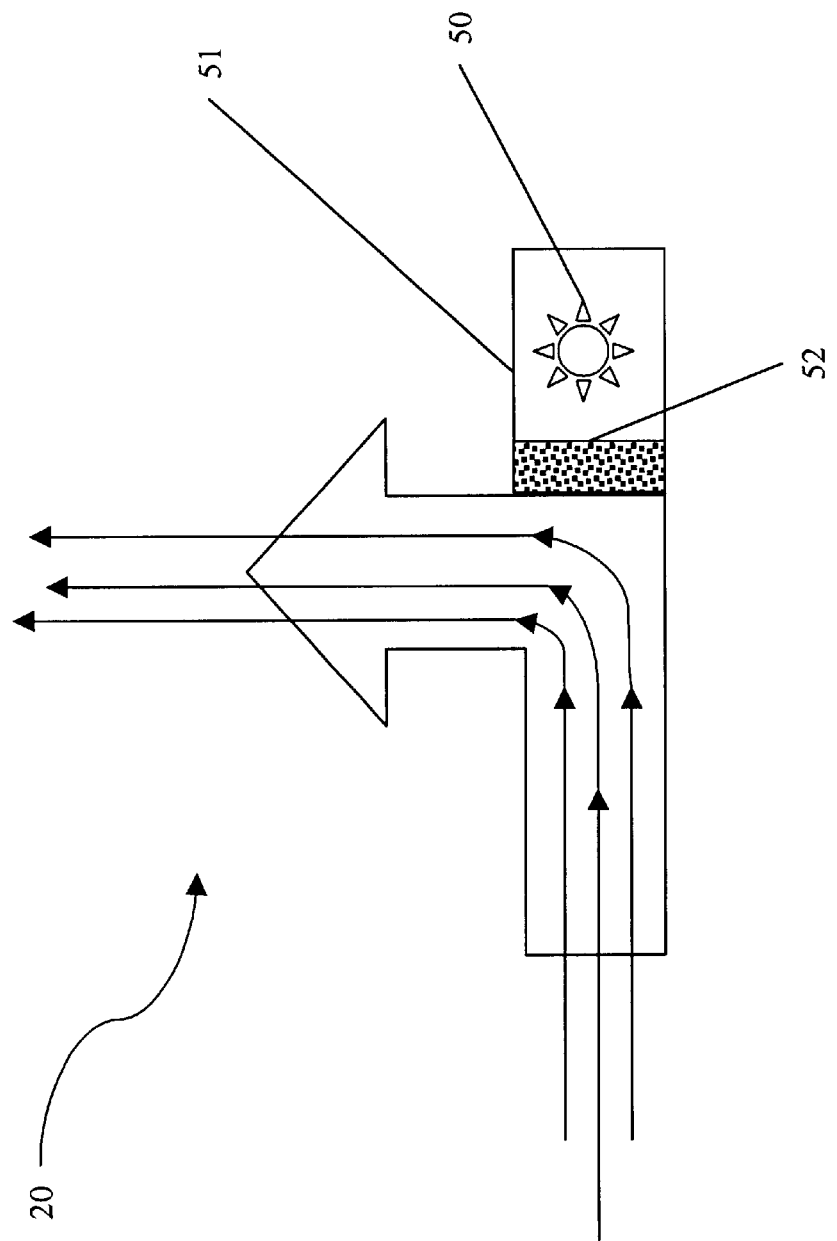
FIG. 2 is a schematic diagram of a blind duct configuration of the present invention.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto. FIG. 1 shows a schematic diagram of a UV air disinfection system, generally described as 10. In the preferred embodiment, a power supply 12 powers a UV light source 14. The UV light source is composed of a UV lamp 15, source optical components 16, and a housing 17. UV light generated by the UV lamp 15 contained within the housing 17 is focused and controlled by the means of the source optical components 16 into at least one UV transmission line 18 that connects to the gas stream purifier 20 at a portal 22, which may alternatively be at least one portal if more than one light input is desired, thus transmitting UV light to the gas. The gas stream purifier portal is equipped with optical components, or portal optics, 32 that further control the UV light at the gas stream purifier 20 in order to provide additional focus and/or control of the UV light for the disinfection of the gas stream (not shown). The gas stream purifier is composed of a dose zone 34 and a housing 36. The dose zone can include a dose delivery device. The dose zone and the housing may be equipped with UV reflective optical components, or interior optics 26, and may also be composed of a UV reflective interior surface and/or coating 28. For longevity as well as UV reflectivity, the interior surfaces may be made of a UV reflective material selected from the group consisting of UV reflective metals and alloys, e.g., stainless steel, aluminum, and the like. Alternatively or additionally, other non-metallic UV reflective materials may be used. Additionally, the contribution of the reflectance of internal surfaces to the efficacy of the system can be capitalized upon by incorporating UV reflective materials and reflection enhancing two- and three-dimensional design into the gas purifier. Moreover, additional surfaces to enhance reflectance may be added to the purifier zone. Additionally, the components, including, but not limited to, particle arresting devices, fiber optic transmission lines, and reflectant surfaces, comprising the gas stream purifier may be manufactured such that they include a photocatalyst that degrades compounds contacting the surface(s) of the gas purifier zone (GPZ). Thus, in one embodiment of the present invention, a particle arrestor is included in the GPZ as the dose delivery device. More particularly, the particle arrestor and other components form an integrated 2- and 3-dimensional design that incorporates UV-reflectant materials, UV-reflectant design, photocatalysts, and additional photocatalyst and reflectant surfaces that advantageously enhance the efficacy of the system.

While generally regarding the UV light source and configuration according to the present invention, the preferred embodiment includes a UV light source that is remotely connectable to the gas stream purifier via at least one fiber optic transmission line. Additionally, the preferred embodiment of the present invention includes at least one optical component positioned between the UV light source and the UV light source system output point. Advantageously, the use of optical components enables the system to maximize the intensity, focus, and control of the UV light rays at the output for any given UV light source or lamp. Also, optical components, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920, which are commonly owned by the assignee of the present invention, and which are incorporated herein by reference in their entirety. Additionally, optical component such as gratings, dichroic filters, focalizers, gradient lenses, gradient reflectors, off-axis lenses, and off-axis reflectors may be used. All UV transmissive optical components included in the present invention are made of UV-transmissive material and all UV-reflective optical components included in the present invention are made of UV-reflective material. The fiber optic lines may include quartz fibers, side-emitting fibers, glass fibers, acrylic fibers, liquid core fibers, hollow-core fibers, core sheath fibers, dielectric coaxial fibers, or a combination of fibers.

With regard to lenses, several embodiments are considered to be within the scope of the present invention. Imaging lenses, such as a parabolic lens, and non-imaging lenses, such as gradient lenses, may be used to focus and control light output. More particularly, a gradient lens collects light through a collecting opening and focuses it to an area smaller than the area of the collecting opening. This concentration is accomplished by changing the index of refraction of the lens along the axis of light transmission in a continuous or semi-continuous fashion, such that the light is "funneled" to the focus area by refraction. An example of gradient lens technology is the Gradium® Lens manufactured by Solaria Corporation. Alternatively, a toroidal reflector, as described in U.S. Pat. No. 5,836,667, is used. In this embodiment, a UV radiation source, such as an arc lamp, is located at a point displaced from the optical axis of a concave toroidal reflecting surface. The concave primary reflector focuses the radiation from the source at an off-axis image point that is displaced from the optical axis. The use of a toroidal reflecting surface enhances the collection efficiency into a small target, such as an optical fiber, relative to a spherical reflecting surface by substantially reducing aberrations caused by the off-axis geometry. A second concave reflector is placed opposite to the first reflector to enhance further the total flux collected by a small target.

Additionally, more than one reflector may be used with a lamp. For example, dual reflectors or three or more reflectors, as taught in U.S. Pat. Nos. 5,706,376 and 5,862,277, maybe incorporated into the preferred embodiment.

Notably, any number of lamps including low pressure, medium pressure, high pressure, and ultra high-pressure lamps, which are made of various materials, e.g., most commonly mercury (Hg) can be used with the system configuration according to the present invention, depending upon the gas or influent characteristics and flow rates through the system. Furthermore, while high and ultra high pressure lamps have not been used commercially to date by any prior art system, predominantly because of the low energy efficiency associated with them and the lack of capacity for prior art design and configuration formulas to include high pressure UV lamps, the present invention is advantageously suited to accommodate medium to high to ultra high pressure lamps, all of which can be metal, halogen, and a combination metal halide. Additionally, spectral calibration lamps, electrodeless lamps, and the like can be used.

In particular, by way of example and not of limitation, one preferred embodiment according to the present invention employs a light pump housing a pencil-type spectral calibration lamp. With a light pump, the number of lamps necessary to treat a given number of gas stream purifiers can be reduced. Also, the lamps are not susceptible to fouling, since they are not exposed to the gas stream to be purified. Furthermore, the maintenance and servicing of the purifier is greatly simplified. The pencil-type spectral calibration lamps are compact and offer narrow, intense emissions, an average intensity that is constant and reproducible, and a longer life relative to other high wattage lamps. Hg (Ar) lamps of this type are generally insensitive to temperature and require only a two-minute warm-up for the mercury vapor to dominate the discharge, then 30 minutes for complete stabilization. A Hg(Ar) UV lamp, which is presently commercially available and supplied by ORIEL Instruments, is used in the preferred embodiment according to the present invention. The ORIEL Hg(Ar) lamp, model 6035, emits UV radiation at 254 nm. When operated at 15 mA using a DC power supply, this lamp emits 74 microwatt/cm2of 254 nm radiation at 25 cm from the source.

Another preferred embodiment according to the present invention employs medium to high-pressure UV lamps, more preferably high-pressure UV lamps. These lamps may include mercury and/or mercury halide lamps, such as Hg(Ar), Hg(Xe), and Hg(Ne).

The light generated by these sources is focused via optics and fibers that are joined by UV-transmissive optical couplers. By way of example and not of limitation, these couplers can be quartz, liquid-filled, hollow, or dielectric coaxial couplers.

The present invention advantageously includes all of the above features, in particular because the UV lamps are separated from the gas purifier and include a light delivery system that incorporates optical components. Without the use of optical components in combination with the UV light source, the intensity of the light could not be effectively focused, directed, and controlled to provide an efficacious disinfection because the UV dosage entering the gas purifier would not be great enough to sterilize the microorganisms. By using optical components incorporated into the gas purifier itself, the gas purifier need be coupled to only one fiber optic transmission line for the supply of UV light. Alternately, the fiber optic transmission line and gas purifier may be simply juxtaposed to allow irradiation of the gas purifier by the light exiting the transmission line or other optics.

The light pump arrangement beneficially extends the lamp life thereby providing a longer replacement time or lamp life cycle. Since turning the lamp off and on degrades the lamp life, the system can be constructed and configured such that other appliances and areas are sterilized intermittently with the gas stream purifier by simply routing the UV light to the device or area to be irradiated. Thus, the lamp need not be turned on and off frequently. However, a timer or other means of system activation can be incorporated into the gas purifier to control exposure.

Advantageously, the gas purification zone has several UV dose regions (not shown) established within it; these UV dose regions are variable, i.e. the greater the distance from the light source introduction at the output area, the lesser the UV light intensity at a particular region, area, or volume. The first region is the proximal light source system exit UV dose region, which occurs at the light source system and gas interface. The next region is the gas interior UV dose region, which occurs in the interior of the gas purifier. This region may be a gas region or a vapor region, i.e., if humidity is introduced, then a vapor region may exist. The last region is the UV surface dose region, which occurs at the interior surface(s) of the gas purifier.

The interior surfaces of the gas purifier may possess photocatalytic properties such that certain reactions are catalyzed in the vicinity of the interior surfaces. These photocatalysts may include the UV-activated, dielectric semiconductors, such as Titanium Oxide; $TiO2$ (photo activation wavelength; not more than 388 nm), Tungsten Oxide; $WO2$ (photo activation wavelength; not more than 388 nm), Zinc Oxide; $ZnO$ (photo activation wavelength; not more than 388 nm), Zinc Sulfide; $ZnS$ (photo activation wavelength; not more than 344 nm) and Tin Oxide; $SnO2$ (photo activation wavelength; not more than 326 nm). In addition to these catalysts, other catalysts, such as $PtTiO_2$, are known and are included as alternative catalysts appropriate for use in the present invention.

For example, $TiO_2$ may be incorporated into surfaces that are made of glass, acrylic, paper, or other appropriate material. When such a surface is irradiated with activating light, fatty acids and other organic chemicals contacting or in close proximity to the surface are chemically degraded, resulting in degradation to smaller volatile products, such as carbon dioxide and water. Additionally, carbon monoxide and other noxious gases are oxidized in such a system. Thus, the incorporation of $TiO_2$ or other photocatalytic material into the interior surface with subsequent irradiation by activating wavelengths reduces the levels of several potential human toxins—organic chemicals, carbon monoxide, and other smoke or combustion byproducts. Advantageously, the disinfected gas purifier is completely free from microorganisms without requiring the addition of chemicals or other additives that would increase the chemical residue on the surface of the gas purifier.

Also, the maximum destruction of microbes, particulate matter, and volatile chemicals depends on several variables. For instance, the UV-TiO2 system does not provide adequate microbial destruction at humidity levels lower than about 40%. On the other hand, there is incomplete deactivation of organisms if the air being treated has a humidity level in excess of 70%. Between about 40% to about 70% humidity—preferably about 50–60%, more preferably about 50% humidity is effective within the system according to the present invention for the deactivation of organisms. Also, without a proper residence time of the contaminated air in the purifier zone, complete disinfection is not obtained. Therefore, single or multi-function gas stream samplers and other devices 42 can be advantageously incorporated in the gas stream before and/or after the gas stream purifier to determine and control such parameters as humidity, temperature, gas partial pressures, and the like. Gases that may be determined include, but are not limited to oxygen, carbon monoxide, carbon dioxide, hydrogen sulfide, sulfur dioxide, hydrogen sulfide, nitrogen oxides, mercaptans, hydrocarbons, methane, and other volatile organic compounds.

UV killing of microbes is dependent on the UV dose, which is a function of light intensity and duration of exposure. The UV dose can thus be increased by increasing the intensity of the UV light or by increasing the exposure time. The exposure time can be increased by decreasing the gas flow velocity in the UV dose zone, increasing the volume of the gas irradiated, or arresting particles in the UV dose zone. An example of an embodiment that increases exposure time by decreasing the gas flow velocity in the UV dose zone is one in which the cross-sectional area of the gas ducting is increased in the UV dose zone. The velocity of the gas will slow due to the increased volume of the duct, and thus will increase the exposure time. An example of an embodiment that increases exposure time by increasing the volume of gas irradiated is one that utilizes an array of fibers along a gas duct to effect irradiation of a length of the gas duct interior, rather than the irradiation of a small section of the gas duct interior. Such an embodiment can be effected by using side-emitting fibers positioned parallel to the gas flow, regular end-emitting fibers distanced along the duct, or fibers with optics that extend the UV irradiation down the length of the gas duct interior. In such embodiments, a light pump device that employs a single lamp and multiple fiber optic transmission lines can significantly reduce the installment and maintenance cost of the system versus a system that uses multiple lamps to achieve an extended exposure area. Finally, particle arrestors maybe inserted into the UV dose zone to increase the UV exposure time. These particle arrestors include, but are not limited to, fiber filters, high-efficiency particle-arresting (HEPA) filters, electrostatic precipitators, cyclone precipitators, and the like. These particle arrestors can include optical components and UV-reflective and photocatalytic properties, such as described previously for the other components of the gas stream purifier, with the resulting benefits. These particle arrestors may also be sized appropriately to fit within an existing gas/HVAC system.

By way of example, and not of limitation, a filter composed of glass fibers coated with TiO2 and undecylenic acid or its derivatives is interposed in the gas stream to arrest and degrade particles and volatiles contained in the gas stream. The filter is irradiated with UV light transmitted by the fiber optic transmission lines to effect the degradation of particles and volatiles and sterilize microorganisms.

The fiber optic transmission lines may be separate from the particle arrestor or may be incorporated into the particle arrestor by weaving, knitting, or non-weaving methods. The particle arrestor may also be manufactured as a multilayered structure to increase the residence time of particles in the surface dose region, thus increasing exposure to UV irradiation and to the photocatalyst incorporated in the particle arrestor. Additionally, the PA fibers may be of a mesh size that increases residence time. Alternately, the PA fibers may be of a mesh size that reduces residence time but that causes less gas pressure drop. Such a mesh size may be desirable in a recirculating type gas purification system. In such a system, the gas will undergo multiple passes through the GPZ. Therefore, a less efficient PA may be adequate because particles that are not trapped in the first pass through the GPZ will eventually be trapped at later passes. If a high gas quality is desired, multiple PAs in series may be used, rather than a single, tight mesh PA. Such a system will be less likely to fail and less expensive to service than a system which incorporates a single, high-efficiency PA. Additionally, such a system can be readily irradiated with a fiber optics-based system that allows routing of the UV light from a single UV light source to the multiple filters.

The filter may be manufactured from a variety of fibers, including, but not limited to, acrylic, glass, quartz, paper, cellulose, cotton and/or other natural and synthetic translucent and non-translucent materials. These fibers may or may not be coated with photocatalysts as described in the preceding.

Although the particle arrestor is designed to be self-cleaning, inorganic materials that do not degrade will accumulate on the filter, eventually fouling it. Therefore, the filter will have to be cleaned or disposed of. In a preferred embodiment, the filter is of an inexpensive design and construction such that it can be disposed of or recycled.

The several advantages of this system include the fact that the remote lamp does not require as extensive cleaning maintenance to remove fouling as a lamp in the interior of the gas purifier may. Additionally, this system allows for reduced maintenance of the purifier due to the self-cleaning aspects of the purifier. Also, the fact that the purifier need be coupled to only one fiber optic transmission line or juxtaposed to the fiber optic transmission line allows for easy replacement of components included in the purifier, such as particle-arresting devices. Finally, the light pump configuration extends the lamp life significantly.

Thus, as can be seen from the advantages of this preferred embodiment according to the present invention, the maintenance required for this preferred embodiment according to the present invention is significantly reduce.

Another preferred embodiment utilizes counter-current irradiation of the gas stream. In this embodiment, a protected counter-current system, the UV irradiation is directed in a parallel fashion against the gas flow. The gas flow is directed away from the UV-emitting device prior to contacting it. For example, in a blind duct configuration, as shown in FIG. 2, the gas is ducted away at 90 degrees from the UV-emitting optical device that is recessed in a blind duct designed to reduce gas circulation around the optical device. Alternately or additionally, the optical device may be protected by a self-cleaning, UV transparent material. Such a configuration effects an increasing dose zone and also reduces fouling of the UV-emitting optical device. This system may be employed when gas turbidity is of such a magnitude that particle arrestor fouling is a major problem and microbial sterilization without particle degradation is considered a sufficient purification of the gas. Alternately, the system can be configured such that the UV light eventually strikes a photocatalytic surface, either for purposes of self-cleaning of the duct and/or other components or for actual degradation of arrested particles. Such an embodiment is easily scalable. For example, the size of the embodiment may extend from a small, portable application with a single point of UV irradiation to a large, whole gas duct system application with multiple points of UV irradiation.

In the preferred embodiment, at least one portal optic is positioned at the portal opening of the gas purifier, between the portal opening and the gas stream purifier or particle arrestor. The function of the at least one portal optic is to control the distribution of UV light in the gas stream purifier in order to enhance the UV disinfecting and degrading capacity of the system. The portal optics may be similar to those described for the source optics, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920 and co-pending applications Ser. Nos. 09/523,609; 09/587,678; which are commonly owned by the assignee of the present invention, and which are incorporated herein by reference in their entirety. Additionally, optical component such as gratings, dichroic filters, focalizers, gradient lenses, and off-axis reflectors may be used. Finally, side-emitting fiber optic transmission lines may be used to distribute the UV light over the filter.

All UV transmissive optical components for the portal optics are made of UV-transmissive material and all UV-reflective optical components for the portal optics are made of UV-reflective material. These optics may extend into the gas stream particle arrestor. For example, fiber optic transmission lines may be incorporated into the gas stream particle arrestor and used to route UV light to the various areas of the gas stream particle arrestor. The fiber optic lines may include quartz fibers, side-emitting fibers, glass fibers, acrylic fibers, liquid core fibers, hollow-core fibers, core sheath fibers, dielectric coaxial fibers, or a combination of fibers. Additionally, the portion of these fibers that extend into the gas stream can be coated with photocatalysts, such that they are self-cleaning. The optics may also be incorporated into the structure of the gas purifier. For example, the interior of the gas purifier before and/or after the particle arrestor may be of a UV reflective material such that UV radiation striking these surfaces is reflected back through the gas stream.

Such a system of UV disinfection can be easily integrated into the gas purifier function cycle by activating the UV light source or allowing irradiation of the gas purifier interior at a predetermined time in an gas stream purifier function cycle. Alternately, the UV disinfection system may be manually activated when desired or may be programmed to activate when gas flow reaches a threshold, for example in natural ventilation systems.

A method for sterilization of the gas stream would consist of providing a gas purifier composed of at least one light source connected by at least one optical connection positioned to provide a focused, controllable light output to the gas purifier, and a control mechanism, thereby producing at least one UV dose zone for the effective sterilization of microorganisms in a gas, activating the UV light source, passing the gas through the gas purifier, thereby providing a sterilized gas stream.

Certain modifications and improvements will occur to those skilled in the art upon a reading of the foregoing description. By way of example, various optical components are used depending upon the particular UV light source or lamp selection for a given system. Moreover, a wide range of applications are contemplated within the scope of the present invention, including application of the UV gas purification system and method to gas purifiers involved in air conditioning, heating, manufacturing, animal rearing, and the like. By way of example, the disinfection of gas stream purifiers, includes, but is not limited to, ventilation systems, discharge systems, manufacturing intake systems, and the like. These gas stream purifiers may be for commercial or household use.

These multiple points of application may also be connected to a single light source, such as a light pump, by light guides. Such an arrangement would eliminate the need for a lamp or light source at every point of application. Because it may not be necessary to continuously irradiate each point of application, such an arrangement would allow the same size lamp as would be require for a single application to service multiple applications intermittently and/or on demand, thus utilizing the lamp more efficiently. Additionally, placing the lamp exterior to the application reduces the risk of glass and/or mercury contaminating the gas stream should the lamp or lamp housing break.

All modifications and improvements have been deleted herein for the sake of conciseness and readability but are properly within the scope of the following claims.

I claim:

1. A gas purification system for the effective sterilization of microorganisms, the system comprising at least one ultraviolet light source disposed within a housing connected by at least one optical connection to a gas stream purifier, wherein the at least one ultraviolet light source is separate from the gas stream purifier, and positioned to provide a focused, controllable light output to the gas stream purifier, and a control mechanism for controlling the at least one UV light source, thereby producing at least one UV dose zone within the gas stream purifier and remote from the at least one UV light source for the effective sterilization of microorganisms in a gas stream passing through the gas stream purifier.

2. The gas purification system according to claim 1, wherein the light source is a light pump including at least one lamp, at least one optic, a housing, and a power supply.

3. The gas purification system according to claim 1, wherein the light source is at least one lamp.

4. The gas purification system according to claim 3, wherein the lamp is a UV lamp.

5. The gas purification system according to claim 4, wherein the UV lamp is a high-pressure lamp.

6. The gas purification system according to claim 4, wherein the UV lamp is a spectral calibration lamp.

7. The gas purification system according to claim 4, wherein the UV lamp is an electrodeless lamp.

8. The gas purification system according to claim 4, wherein the UV lamp is a mercury halide lamp.

9. The gas purification system according to claim 4, wherein the UV lamp emits light in the UVV and UVC wavelengths.

10. The gas purification system according to claim 4, wherein the light source includes at least one light source optical component positioned to provide a focused, controllable light output to a gas purifier.

11. The gas purification system according to claim 10, wherein the light source optical component is UV transmissive.

12. The gas purification system according to claim 10, wherein the light source optical component is UV reflective.

13. The gas purification system according to claim 10, wherein the at least one light source optical component is a reflector and/or a lens.

14. The gas purification system according to claim 1, wherein the at least one optical connection is a fiber optic transmission line.

15. The gas purification system according to claim 14, wherein the fiber optic transmission line is removably connectable to the light source and the gas purifier.

16. The gas purification system according to claim 14, wherein the fiber optic transmission line is selected from the group of fiber optic transmission lines including acrylic lines, glass lines, liquid core lines, quartz lines, hollow core lines, core-sheath lines, dielectric coaxial lines, and combination thereof.

17. The gas purification system according to claim 1, wherein the gas purifier includes a dose zone and a gas purifier housing.

18. The gas purification system according to claim 17, wherein the gas purifier housing is UV reflective.

19. The gas purification system according to claim 17, wherein the dose zone includes a portal for removable connection to a fiber optic transmission line.

20. The gas purification system according to claim 19, further including at least one portal optical component positioned between the portal opening and the interior of the gas purifier.

21. The gas purification system according to claim 20, wherein the at least one portal optical component is UV transmissive.

22. The gas purification system according to claim 20, wherein the at least one portal optical component is UV reflective.

23. The gas purification system according to claim 20, wherein the at least one portal optical component is a reflector and/or a lens.

24. The gas purification system according to claim 17, wherein the dose zone includes a delivery device.

25. The gas purification system according to claim 24, wherein the delivery device includes at least one light emitter selected from the group consisting of side-emitting fiber optic transmission lines, end-emitting fiber optic transmission line, and combinations thereof.

26. The gas purification system according to claim 24, wherein the delivery device further includes at least one particle arrestor.

27. The gas purification system according to claim 26, wherein the at least one particle arrestor is a fiber filter.

28. The gas purification system according to claim 27, wherein the fiber filter is composed of fibers selected from the group consisting of glass fibers, acrylic fibers, quartz fibers, paper fibers, cellulose fibers, cotton fibers, plastic fibers, and combinations thereof.

29. The gas purification system according to claim 27, wherein the fiber filter is manufactured in a method selected from the group consisting of non-woven, woven, and knitted methods, including multi-layer structure.

30. The gas purification system according to claim 27, wherein the fiber filter is disposable.

31. The gas purification system according to claim 24, wherein the delivery device further includes at least two particle arrestors in series.

32. The gas purification system according to claim 24, wherein the delivery device includes catalytic surfaces.

33. The gas purification system according to claim 32, wherein the catalytic surfaces are self-cleaning.

34. The gas purification system according to claim 32, wherein the catalytic surfaces are photocatalytic surfaces containing at least one photocatalyst.

35. The gas purification system according to claim 34, wherein the at least one photocatalyst is a light-activated, dielectric semiconductor.

36. The gas purification system according to claim 34, wherein the at least one photocatalyst is selected from the group consisting of $TiO_2$, $WO_2$, ZnO, ZnS, $SnO_2$, $PtTiO_2$, and combinations thereof.

37. The gas purification system according to claim 1, wherein at least one interior surface of the gas purifier is a UV reflective surface.

38. The gas purification system according to claim 37, wherein the at least one UV reflective surface is selected from the group consisting of stainless steel, aluminum, and combinations thereof.

39. The gas purification system according to claim 1, wherein the interior of the gas purifier includes at least one interior optical component that is attached to the interior surfaces.

40. The gas purification system according to claim 39, wherein the at least one interior optical component is UV transmissive.

41. The gas purification system according to claim 39, wherein the at least one interior optical component is UV reflective.

42. The gas purification system according to claim 39, wherein the at least one interior optical component is a reflector and/or a lens.

43. The delivery device of claim 24, further providing UV irradiation countercurrent to the gas flow.

44. The delivery device of claim 43, wherein the delivery device is protected from the gas flow.

45. The delivery device of claim 43, wherein the protection is a shield.

46. The delivery device of claim 43, wherein the delivery device is outside the gas flow.

47. The delivery device of claim 46, wherein the delivery device is in a blind duct configuration wherein the gas is ducted away at 90 degrees from a UV-emitting optical device, which is recessed in a blind duct designed to reduce gas circulation around the optical device.

48. A gas purifier for the effective sterilization of microorganisms in a gas, the gas purifier including a dose zone and housing, thereby producing at least one dose region for the effective sterilization of microorganisms in a gas.

49. The gas purifier system according to claim 48, wherein the housing is UV reflective.

50. The gas purifier according to claim 48, wherein the housing includes a portal proximal to the dose zone for removable connection to a fiber optic transmission line.

51. The gas purifier according to claim 50, further including at least one portal optical component positioned between the portal and the interior of the gas purifier.

52. The gas purifier according to claim 51, wherein the at least one portal optical component is UV transmissive.

53. The gas purifier according to claim 51, wherein the at least one portal optical component is UV reflective.

54. The gas purifier according to claim 51, wherein the at least one portal optical component is a reflector and/or a lens.

55. The gas purifier according to claim 48, wherein the dose zone further includes a delivery device.

56. The gas purifier according to claim 55, wherein the delivery device includes at least one light emitter selected from the group consisting of side-emitting fiber optic transmission lines, end-emitting fiber optic transmission line, and combinations thereof.

57. he gas purifier according to claim 55, wherein the delivery device further includes at least one particle arrestor.

58. The gas purifier according to claim 57, wherein the at least one particle arrestor is a fiber filter.

59. The gas purifier according to claim 58, wherein the fiber filter is composed of fibers selected from the group consisting of glass fibers, acrylic fibers, quartz fibers, paper fibers, cellulose fibers, cotton fibers, plastic fibers, and combinations thereof.

60. The gas purifier according to claim 58, wherein the fiber filter is manufactured in a method selected from the group consisting of non-woven, woven, and knitted methods, including multi-layer structure.

61. The gas purifier according to claim 58, wherein the fiber filter is disposable.

62. The gas purification system according to claim 57, wherein the delivery device further includes at least two particle arrestors in series.

63. The gas purifier according to claim 55, wherein the delivery device includes catalytic surfaces.

64. The gas purifier according to claim 63, wherein the catalytic surfaces are self-cleaning.

65. The gas purifier according to claim 63, wherein the catalytic surfaces are photocatalytic surfaces containing at least one photocatalyst.

66. The gas purifier according to claim 65, wherein the at least one photocatalyst is a light-activated, dielectric semiconductor.

67. The gas purifier according to claim 65, wherein the at least one photocatalyst is selected from the group consisting of $TiO_2$, $WO_2$, ZnO, ZnS, $SnO_2$, $PtTiO_2$, and combinations thereof.

68. The gas purifier according to claim 55, wherein at least one interior surface of the gas purifier is a UV reflective surface.

69. The gas purifier according to claim 68, wherein the at least one UV reflective surface is selected from the group consisting of stainless steel, aluminum, and combinations thereof.

70. The gas purifier according to claim 55, wherein the interior of the gas purifier includes at least one interior optical component that are attached to the interior surfaces.

71. The gas purifier according to claim 70, wherein the at least one interior optical component is UV transmissive.

72. The gas purifier according to claim 70, wherein the at least one interior optical component is UV reflective.

73. The gas purifier according to claim 70, wherein the at least one interior optical component is a reflector and/or a lens.

74. A method for the purification of a gas, comprising the steps of: providing a gas purifier comprising at least one ultraviolet light source disposed within a housing connected by at least one optical connection to a gas stream purifier, wherein the at least one ultraviolet light source is separate from the gas stream purifier, and positioned to provide a focused, controllable light output to the gas stream purifier, and a control mechanism for controlling the at least one UV light source, thereby producing at least one UV dose zone within the gas stream purifier and remote from the at least one UV light source for the effective sterilization of microorganisms in a gas, activating the UV light source, passing the gas through the gas purifier, thereby providing a sterilized gas stream.

* * * * *